United States Patent
Mitra et al.

(10) Patent No.: US 9,773,200 B2
(45) Date of Patent: Sep. 26, 2017

(54) MINIATURE INTEGRATED SENSOR CIRCUIT

(71) Applicant: IMEC VZW, Leuven (BE)

(72) Inventors: Srinjoy Mitra, Leuven (BE); Tom Torfs, Kraainem (BE)

(73) Assignee: IMEC VZW, Leuven (BE)

( * ) Notice: Subject to any disclaimer, the term of this patent is extended or adjusted under 35 U.S.C. 154(b) by 0 days.

(21) Appl. No.: 14/975,435

(22) Filed: Dec. 18, 2015

(65) Prior Publication Data

US 2016/0180211 A1    Jun. 23, 2016

(30) Foreign Application Priority Data

Dec. 18, 2014  (EP) ..................... 14198799

(51) Int. Cl.
*G06K 19/077* (2006.01)
*G01N 27/02* (2006.01)
*G01N 33/483* (2006.01)

(52) U.S. Cl.
CPC ....... *G06K 19/07749* (2013.01); *G01N 27/02* (2013.01); *G01N 33/483* (2013.01)

(58) Field of Classification Search
USPC ........................ 235/492; 438/261; 600/345
See application file for complete search history.

(56) References Cited

U.S. PATENT DOCUMENTS

| | | | | |
|---|---|---|---|---|
| 2003/0152766 A1* | 8/2003 | Vargo | ........................ | B32B 7/12 428/343 |
| 2007/0145966 A1* | 6/2007 | Shekhawat | .......... | G01N 29/036 324/71.1 |
| 2009/0146812 A1* | 6/2009 | Rice | .................. | G06K 19/0723 340/572.1 |
| 2011/0051375 A1* | 3/2011 | Ammar | ................. | H01L 23/552 361/728 |
| 2013/0306740 A1* | 11/2013 | Mathews | ............... | G06K 19/02 235/492 |
| 2014/0073071 A1* | 3/2014 | Diorio | ................ | G06K 19/0723 438/26 |
| 2014/0336485 A1* | 11/2014 | Mujeeb-U-Rahman | | A61B 5/1473 600/345 |

OTHER PUBLICATIONS

Usami, Mitsuo et al., "A 0.05x0.05mm RFID Chip with Easily Scaled-Down ID-Memory", 2007 IEEE International Solid-State Circuits Conference, 2007, pp. 482-483.
Tsai, Tsung-Hsun et al., "Analysis of Dynamic Range, Linearity, and Noise of a Pulse-Frequency Modulation Pixel", IEEE Transactions on Electron Devices, vol. 59, No. 10, Oct. 2012, pp. 2675-2681.
Mandecki, W. et al., "Microtransponders, the Miniature RFID Electronic Chips, as Platforms for Cell Growth in Cytotoxicity Assays", 2006 International Society for Analytical Cytology, 2006, pp. 1-9.
Bai, Shun et al., "A Simple Voltage Reference With Ultra Supply Independency", 2012 IEEE International Symposium on Circuits and Systems (ISCAS), 2012, pp. 2829-2832.

* cited by examiner

*Primary Examiner* — Allyson Trail
(74) *Attorney, Agent, or Firm* — McDonnell Boehnen Hulbert & Berghoff LLP

(57) ABSTRACT

A miniature integrated CMOS sensor circuit comprising a time domain ADC module, a digital logic and control module, a data transmitter module, a power circuit module, a voltage reference module, an identification code tag, and an RF coil disposed within an area of less than 0.1 mm².

12 Claims, 6 Drawing Sheets

MINIATURE INTEGRATED SENSOR CIRCUIT

CROSS-REFERENCE TO RELATED APPLICATION

This application claims priority to European Patent Application No. 14198799 filed on Dec. 18, 2014, the contents of which are hereby incorporated by reference.

TECHNICAL FIELD

The present description relates generally to sensor circuits, and more specifically to a miniature integrated sensor circuit.

BACKGROUND

Miniaturization of sensor circuits has become an important challenge. RFID tags, for instance, generally require coils external to the chip (although, some versions exist with coils integrated with the chip) for operation at short range. In one example, a small RFID chip measures 50 µm×50 µm and includes a post-processed coil, as described in "A 0.05×0.05 mm2 RFID Chip with Easily Scaled-Down ID-Memory," by M. Usami et al., Solid-State Circuits IEEE International Conference—ISSCC, pp. 482-483, 2007.

Some circuits for photometric imaging applications, such as the circuits described in "Analysis of Dynamic Range, Linearity, and Noise of a Pulse-Frequency Modulation Pixel," by Tsung-Hsun Tsai et al., IEEE Transactions On Electron Devices, Vol. 59, No. 10, pp. 2675-2681, July 2012, do not have a complete self-contained circuit inside the small area of the sensor. These circuits depend on a stable reference and power supply available from outside the sensor area.

Some biosensor modules use a fluorescent sensing mechanism and are powered by light, and may be as small as 250 µm×250 µm, as described in "Microtransponders, the miniature RFID electronic chips, as platforms for cell growth in cytotoxicity assays," by W. Mandecki et al., 2006 International Society for Analytical Cytology, pp. 1097-1105. These biosensor modules, however, only transmit an identification code and do not contain any sensor readout mechanism on chip. Further, these modules rely on an external unit to read out the fluorescent sensor signal optically, which limits the transduction mechanism to photometric and limit the types of molecules that can be sensed.

There is a motivation to further miniaturize current sensor circuits in order to enable further applications.

SUMMARY

According to one aspect of the present description, there is provided a miniature integrated CMOS sensor circuit that has an area of less than 0.1 mm². In one example, such a miniature CMOS sensor circuit is implemented within a circle having a diameter of 0.35 mm.

According to an example embodiment, a novel circuit architecture is developed which advantageously includes a large functionality in a small IC area. The functionality includes digital logic and control, a timing mechanism, a power mechanism, a communication mechanism to transmit the results to an outside receiver, and an addressing/identification mechanism to identify each sensor or sensor type and to coordinate communications to avoid data loss due to collisions.

According to an example embodiment, the new miniature integrated sensor circuit comprises active sensing elements.

According to an example embodiment, the new miniature integrated sensor circuit operates with very low power.

According to an example embodiment, there is provided a miniature integrated sensor circuit that includes a time domain ADC module, a digital logic and control module, a data transmitter module, a power circuit module, a voltage reference module, an identification code tag, and an RF coil disposed within an area of less than 0.1 mm².

According to an example embodiment, the miniature integrated sensor circuit further comprises a functionalization layer module configured for a particular sensing application and to perform transducer functions.

According to an example embodiment, the miniature integrated sensor circuit is configured for one or more of photometric, impedimetric, or amperometric active sensing.

According to an example embodiment, the time domain ADC module is configured for providing pulse frequency modulated or pulse width modulated signals.

According to an example embodiment, there is provided a biosensing device comprising at least one miniature integrated sensor circuit according to embodiments herein described.

Advantageously, such integrated sensor circuit may be used as part of an active and compact biosensing device, which can be inserted into biological samples. For example, large arrays of such miniature biosensor modules, each detecting a specific biological parameter, can provide useful information about the composition and other parameters of biological samples.

According to an example embodiment, the RF coil is configured for receiving power and for telemetry communication with an external device unit.

According to an example embodiment, the power circuit module and the voltage reference module are configured for generating a stable reference voltage from the power received by the RF coil.

According to an example embodiment, the miniature integrated sensor circuit is further configured for deriving a periodic clock signal from a signal received from an external device unit and/or from the stable reference voltage.

According to an example embodiment, the time-domain ADC module uses a current reference, a voltage reference, and a comparator for providing a digital output. In this example, the digital output is the output of the comparator and the output representing the digital value of a sensed signal to be converted by the ADC module.

According to an example embodiment, the time-domain ADC module is configured for converting an electrical current into a saw-tooth wave of varying frequency, and the conversion into a digital value output is performed by measuring the frequency of the saw-tooth wave and/or its period.

According to an example embodiment, the time-domain ADC module is configured for photometric, impedimetric, and/or amperometric active sensing.

According to an example embodiment, the time-domain ADC module further comprises a plurality of electronic switches that can be activated/deactivated for selecting the active sensing type.

According to an example embodiment, the miniature integrated sensor circuit further comprises an identification code that identifies a type of sensed parameter, sensitivity, and other parameters. In this example, the circuit is configured for transmitting this identification code with all sensed data through the RF coil to the external device unit.

In a further embodiment, the miniature integrated sensor circuit is integrated in a CMOS chip.

BRIEF DESCRIPTION OF THE DRAWINGS

The above and other aspects of the circuit according to the present description will be shown and explained with reference to the non-restrictive example embodiments described hereinafter.

DETAILED DESCRIPTION

In the following description of example embodiments, various features may be grouped together in a single embodiment, figure, or description thereof for the purpose of streamlining the disclosure and aiding in the understanding of one or more of the various inventive aspects. This is, however, not to be interpreted as the invention requiring more features than the ones expressly recited in the claims. Furthermore, combinations of features of different embodiments are meant to be within the scope of the invention, as would be clearly understood by those skilled in the art. Additionally, in other instances, well-known methods, structures and techniques have not been shown in detail in order not to obscure the conciseness of the description.

Figure 1:
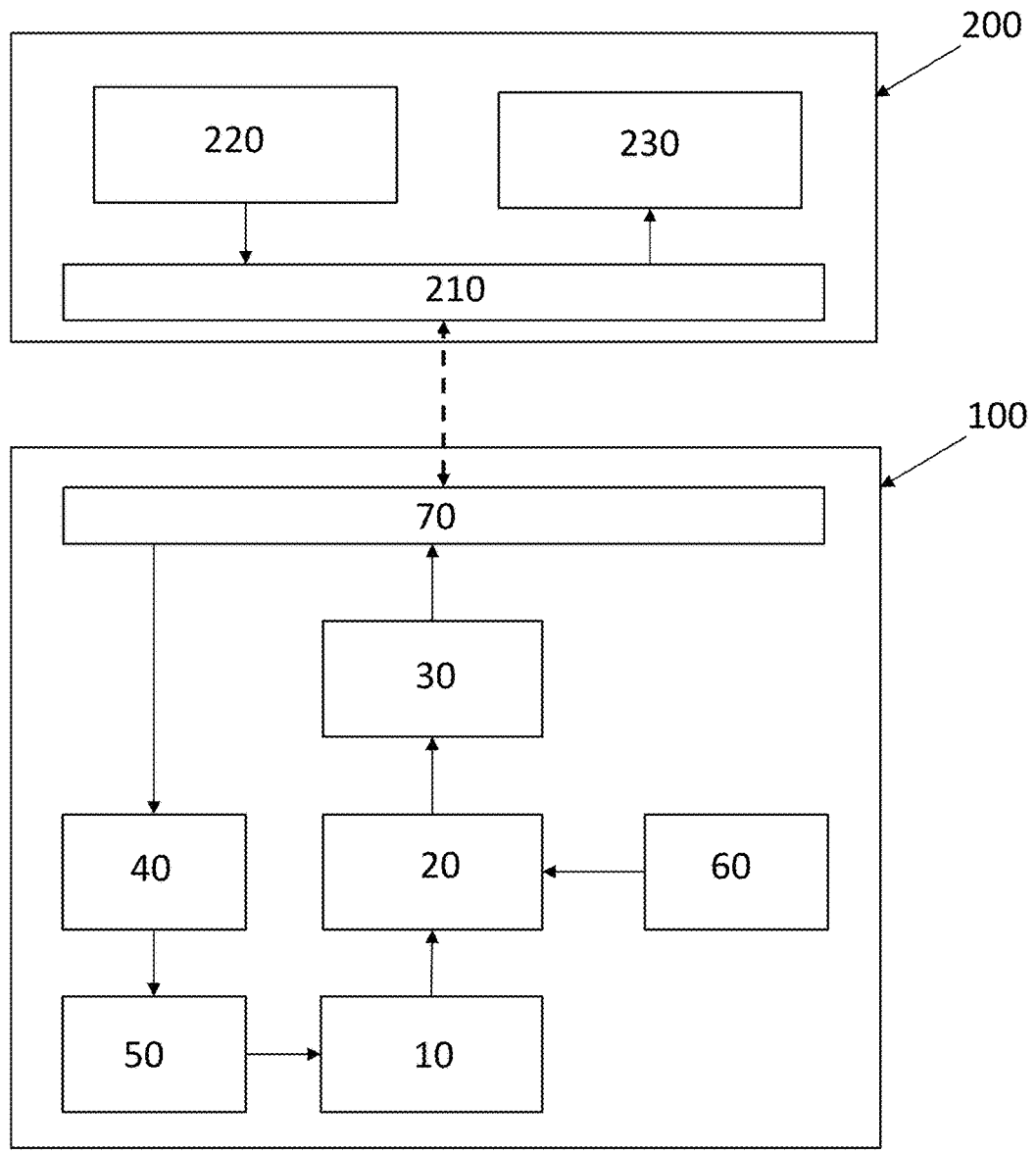
FIG. 1 shows a first general block diagram of an example miniature integrated CMOS sensor circuit.

FIG. 1 shows a first general block diagram of an example miniature integrated sensor circuit 100, comprising a time domain ADC module 10, a digital logic and control module 20, a data transmitter module 30, a power circuit module 40, a voltage reference module 50, an identification code tag 60 and an RF coil 70. According to an example embodiment, the RF coil may be used for receiving power and for telemetry communication with an external unit 200. In this example, the external unit comprises an external RF coil 210, an RF transmitter module 220, and an RF receiver module 230.

Figure 2:
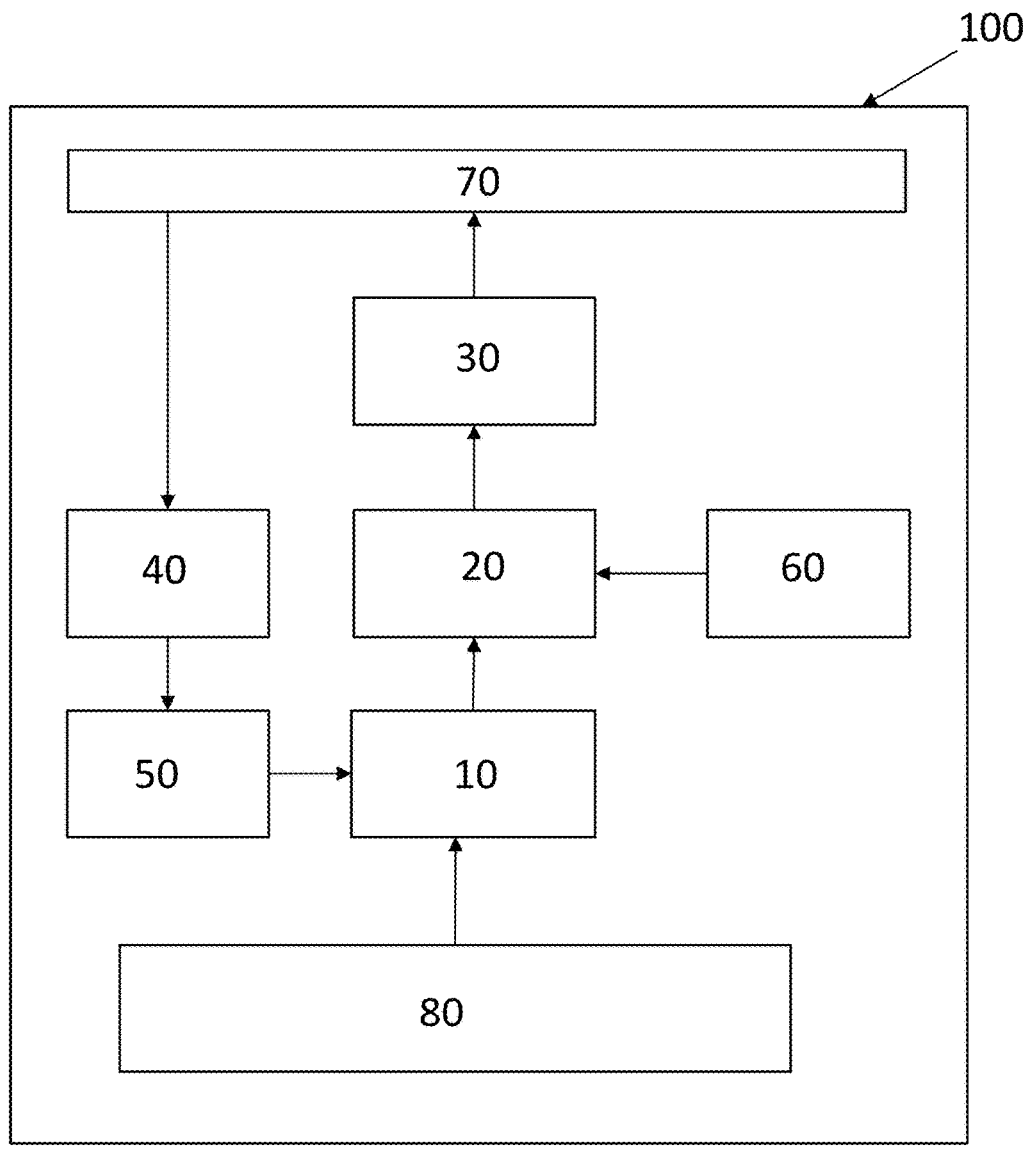
FIG. 2 shows a second general block diagram of an example miniature integrated CMOS sensor circuit.

FIG. 2 shows a second general block diagram of an example miniature integrated sensor circuit 100, further comprising a functionalization layer module 80 configured for a particular sensing application and transducer functions (e.g. conversion to an electrical signal).

Illustratively, such complex embodiments of the miniature integrated sensor circuit 100 are implemented in a chip with a size of less than 0.1 mm$^2$. According to an example embodiment, the miniature integrated sensor circuit 100 presents an advantageous combination of a time-domain ADC with a very small voltage reference and an inductive link for power/telemetry. In this example, the time-domain ADCs have a complete self-contained circuit inside the tiny area of the sensor.

Figure 3:
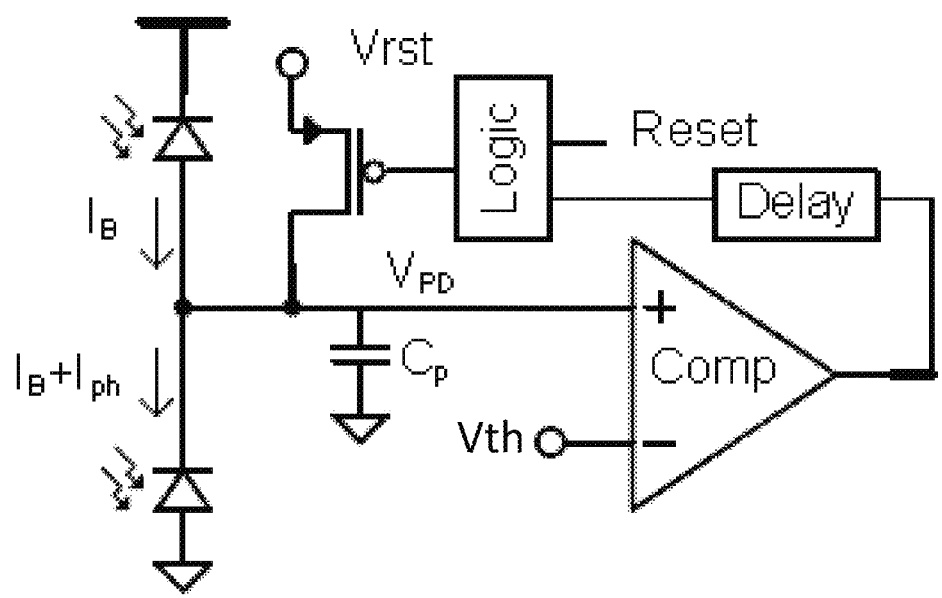
FIG. 3 shows a photometric active sensing circuit according to an example embodiment.
Figure 4:
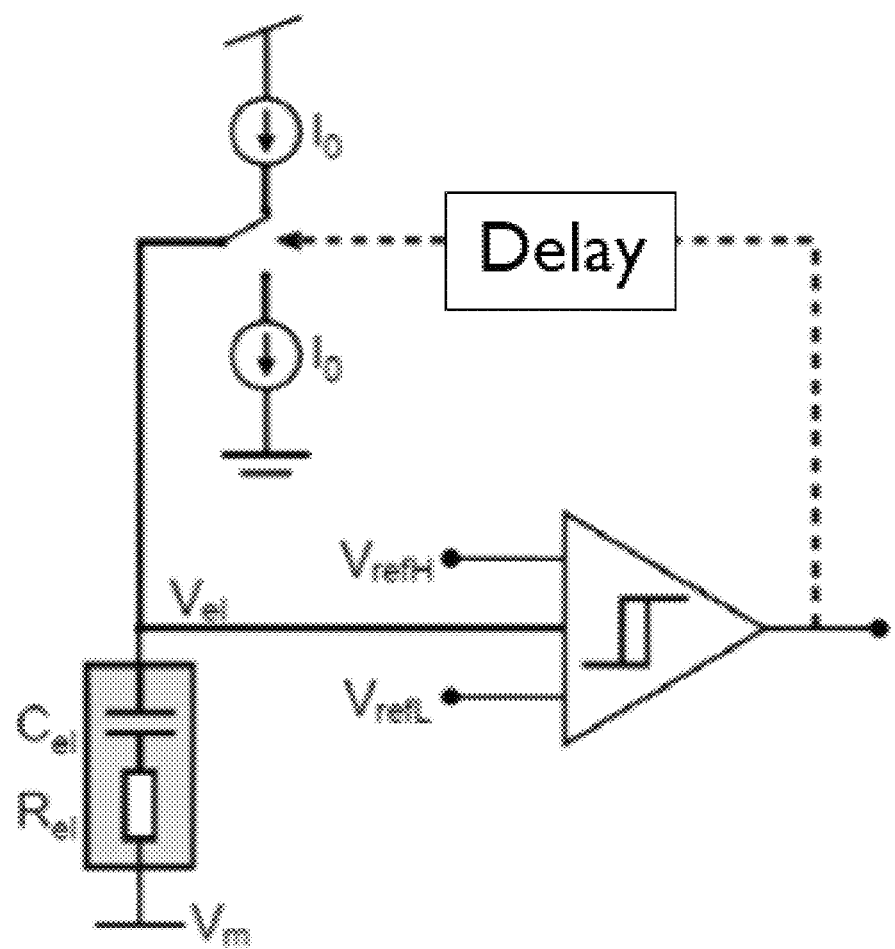
FIG. 4 shows an impedimetric active sensing circuit according to an example embodiment.
Figure 5:
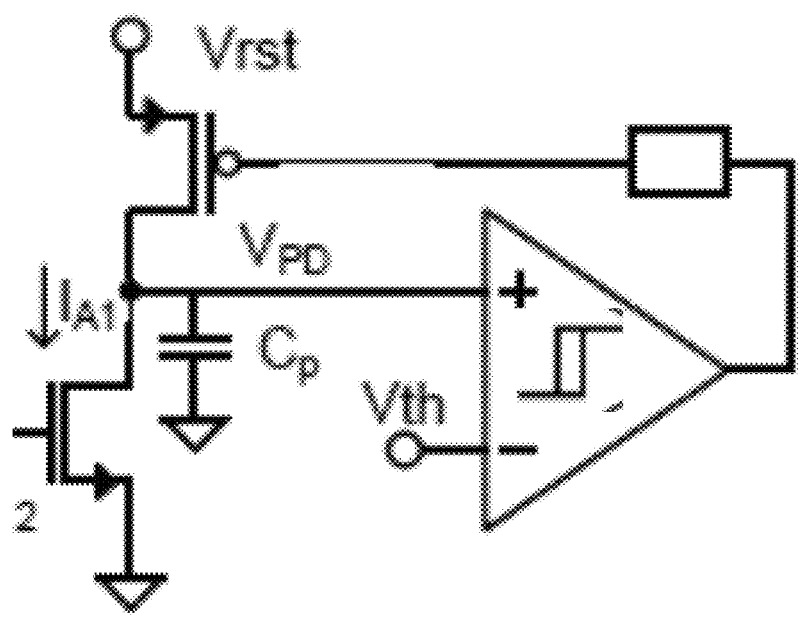
FIG. 5 shows an amperometric active sensing circuit according to an example embodiment.
Figure 6:
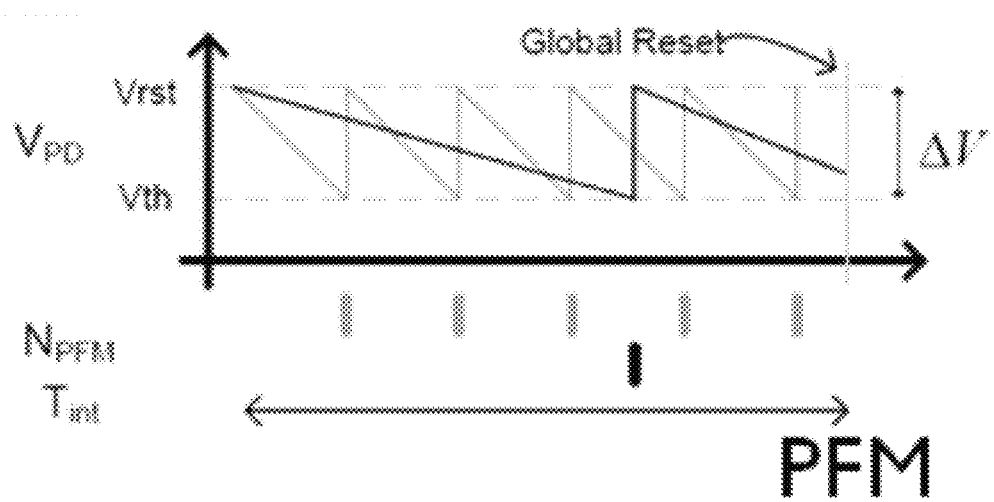
FIG. 6 shows a graph of a pulse frequency modulated (PFM) signal at the output of a comparator in an active sensing circuit according to an example embodiment.
Figure 7:
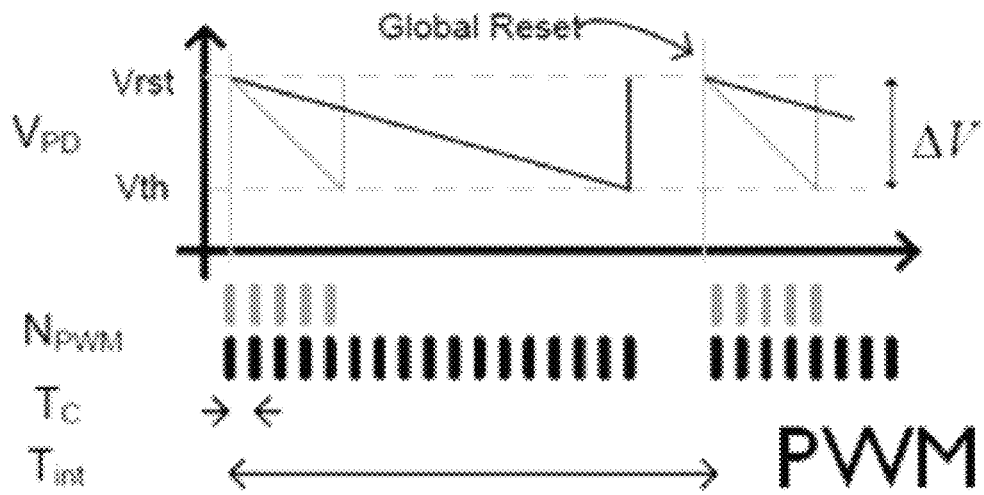
FIG. 7 shows a graph of a pulse width modulated (PWM) signal at the output of a comparator in an active sensing circuit according to an example embodiment.

The time-domain ADC module 10 can be adapted for different transducing mechanisms, for example, FIG. 3 shows a photometric active sensing circuit, FIG. 4 shows an impedimetric active sensing circuit, and FIG. 5 shows an amperometric active sensing circuit. Such circuits make use in particular of a voltage reference, a current reference, and a comparator. The output of the comparator represents the digital value of the signal. The circuits convert the electrical input current into a saw-tooth wave of varying frequency. The conversion into digital information can be performed either by measuring the frequency of the saw-tooth wave (a PFM approach as shown in FIG. 6) or by measuring its period (a PWM approach as shown in FIG. 7).

One issue that traditionally prevents completely integrating such an ADC in a very small area is that the circuit needs an accurate reference voltage for the comparator, and also an accurate and stable high frequency clock for the PFM or PWM measurement or to do logical operations to transmit the counted values. According to an example embodiment, in order to create a stable reference voltage from an unstable (highly varying) inductive powered supply, the time domain ADC is combined with an ultra-small voltage source using native transistors, such as the one disclosed in document "A simple voltage reference with ultra supply independency," by Shun Bai and Stan Skafidas, 2012 IEEE International Symposium on Circuits and Systems (ISCAS), pp. 2829-2832, 2012. This consumes the least possible area and is independent of around 200% supply variation. Most of the generic circuit blocks (references and oscillators) may be derived from such ultra-small voltage source.

According to an example embodiment, an accurate clock may be provided over the inductive link from the external unit 200, in order to provide a stable high frequency clock needed for the PFM or PWM. According to an example embodiment, a stable reference voltage may be used to create an accurate clock.

Due to the small circuit size restrictions, the ADC may be limited in achievable dynamic range. This is addressed in an embodiment in which during the post-CMOS processing that is performed to include the sensor functionalization layer module 80, additional conductive connections are placed on the CMOS circuit which can configure the range and other parameters of the circuit so that the ADC covers the dynamic range that is expected for the particular application (depending on the functionalization layer module 80 provided). In this way the same CMOS circuit with limited dynamic range can cover a much larger required dynamic range and measure different types of physical parameters and support different sensor functionalization layers with different sensitivities.

According to an example embodiment, a post-processing configuration method is also used to put a unique or quasi-unique identification code (e.g. an RF tag) on each circuit so that each sensor can be identified during transmission of its data. The (quasi-)unique identification of the sensor circuit then can be combined with a database that keeps track of the sensed parameters and other circuit parameters corresponding to each sensor circuit in order to interpret the results.

According to another example embodiment, a post-processing configuration method is used to associate an identification code with one or more of the sensor modules. In this example, the identification code identifies the type of sensed parameter, sensitivity, and other parameters so that these can be included in the transmission of data. In this embodiment it is not necessary to (quasi-)uniquely identify each sensor module, but it is sufficient to identify the sensed parameter, sensitivity, and the like so that the output data can be properly interpreted.

According to another example embodiment, a post-processing configuration method is also used to reconfigure the analogue front-end electronics to select between the different transduction mechanisms (photometric, impedimetric, and/or amperometric). As shown in FIGS. 3, 4, and 5, with minor adaptations the time-domain ADC-based read-out mechanism can be configured to measure photometric, impedimetric, and/or amperometric changes. According to an example embodiment, the sensor circuit is reconfigured for these different mechanisms using electronic switches which are controlled by the post-processing configuration. This allows more flexibility in deciding the sensing mechanism during the post-processing stage when the sensor functionalization is applied, at the cost of a small increase in area.

We claim:

1. A miniature integrated CMOS sensor circuit comprising:
    disposed within an area of less than 0.1 mm$^2$, a time-domain ADC module, a digital logic and control module, a data transmitter module, a power circuit module, a voltage reference module, an identification code tag, and an RF coil,
    wherein the RF coil is configured to receive power from and for telemetry communication with an external device unit,
    wherein the power circuit module and the voltage reference module are configured to generate a stable reference voltage from the power received by the RF coil,
    and wherein the sensor circuit is configured to derive a periodic clock signal from a signal received from the external device unit or from the stable reference voltage.

2. The miniature integrated CMOS sensor circuit according to claim 1, further comprising a functionalization layer module configured for a particular sensing application and to perform transducer functions.

3. The miniature integrated CMOS sensor circuit according to claim 1, wherein the time-domain ADC module is configured to use a current reference, a voltage reference, and a comparator to provide a digital output, wherein the digital output is the output of the comparator, and the output represents a digital value of a sensed signal to be converted by the ADC module.

4. The miniature integrated CMOS sensor circuit according to claim 3, wherein the time-domain ADC module is configured to convert an electrical current into a saw-tooth wave of varying frequency, wherein the conversion into a digital value output includes measuring the frequency or period of the saw-tooth wave, wherein measuring the frequency or period of the saw-tooth wave utilizes the periodic clock signal.

5. The miniature integrated CMOS sensor circuit according to claim 1, wherein one or more of the modules is associated with an identification code that identifies at least one of a type of sensed parameter or sensitivity, and wherein the data transmitter module is configured to transmit this identification code with all sensed data through the RF coil to the external device unit.

6. The miniature integrated CMOS sensor circuit according to claim 1, wherein the identification code tag is an RF tag.

7. The miniature integrated CMOS sensor circuit according to claim 1, wherein the time-domain ADC module is configured for at least one of photometric, impedimetric, or amperometric active sensing type.

8. The miniature integrated CMOS sensor circuit according to claim 7, wherein the time-domain ADC module comprises a plurality of electronic switches that are configured to be activated/deactivated to select the active sensing type.

9. A biosensing device comprising at least one miniature integrated CMOS sensor circuit according to claim 1.

10. A miniature integrated CMOS sensor circuit comprising:
    disposed within an area of less than 0.1 mm$^2$, a time-domain ADC module, a digital logic and control module, a data transmitter module, a power circuit module, a voltage reference module, an identification code tag, and an RF coil,
    wherein the time-domain ADC module is configured to use a current reference, a voltage reference, and a comparator to provide a digital output, wherein the digital output is the output of the comparator, and the digital output represents a digital value of a sensed signal to be converted by the ADC module.

11. A miniature integrated CMOS sensor circuit comprising:
    disposed within an area of less than 0.1 mm$^2$, a time-domain ADC module, a digital logic and control module, a data transmitter module, a power circuit module, a voltage reference module, an identification code tag, and an RF coil,
    wherein the time-domain ADC module is configured to convert a sensed signal into a digital output by converting the sensed signal into a saw-tooth wave of varying frequency and measuring a frequency or period of the saw-tooth wave.

12. The miniature integrated CMOS sensor circuit according to claim 11,
    wherein the RF coil is configured to receive power from and for telemetry communication with an external device unit,
    wherein the power circuit module and the voltage reference module are configured to generate a stable reference voltage from the power received by the RF coil,
    wherein the sensor circuit is configured to derive a periodic clock signal from the stable reference voltage,
    and wherein measuring the frequency or period of the saw-tooth wave utilizes the periodic clock signal.

* * * * *